United States Patent [19]
Guthrie et al.

[11] 3,966,772
[45] June 29, 1976

[54] CITRIC ACID DERIVATIVES

[75] Inventors: Robert William Guthrie, Fairfield; James Guthrie Hamilton, Nutley; Richard Wightman Kierstead, North Caldwell; O. Neal Miller, Montclair, all of N.J.; Ann Clare Sullivan, New York, N.Y.

[73] Assignee: Hoffmann-La Roche Inc., Nutley, N.J.

[22] Filed: Feb. 13, 1974

[21] Appl. No.: 442,258

Related U.S. Application Data

[62] Division of Ser. No. 204,334, Dec. 2, 1971, Pat. No. 3,810,931.

[52] U.S. Cl. .............................. 260/348 A; 424/278
[51] Int. Cl.$^2$ ........................................ C07D 303/38
[58] Field of Search .............................. 260/348 A

[56] References Cited
UNITED STATES PATENTS

| | | | |
|---|---|---|---|
| 2,475,629 | 7/1949 | Meincke | 424/313 |
| 3,156,709 | 11/1964 | Allan | 260/348.5 L |
| 3,717,611 | 2/1973 | Baumer et al. | 260/348 A |

FOREIGN PATENTS OR APPLICATIONS

| | | | |
|---|---|---|---|
| 633,354 | 12/1961 | Canada | 260/348.5 L |

OTHER PUBLICATIONS

F. C. Magne et al., I & EC, vol. 45, No. 7 (1953), pp. 1546–1547.

F. P. Greenspan et al., I & EC, vol. 45, No. 12 (1953), pp. 2722–2726.

Chemical Abstracts, vol. 54 (1960), 14214–14215.

*Primary Examiner*—Norma S. Milestone
*Attorney, Agent, or Firm*—Samuel L. Welt; George M. Gould; Raymond R. Wittekind

[57] ABSTRACT

Epoxyaconitic acid and esters thereof are useful for the control of lipogenesis.

3 Claims, No Drawings

CITRIC ACID DERIVATIVES

This is a division of application Ser. No. 204,334 filed Dec. 2, 1971 now U.S. Pat. No. 3,810,931.

BRIEF DESCRIPTION OF THE INVENTION

The present invention relates to novel epoxides of the formula

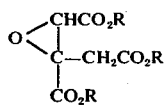

wherein all R groups are either hydrogen or the same lower alkyl;
and the stereoisomers, optical antipodes and pharmaceutically acceptable salts thereof, which compounds inhibit fatty acid synthesis in biological systems and are thus useful in the treatment of obesity and in correcting conditions of lipid abnormalities.

As used throughout the specification and the appended claims, the term "lower alkyl" shall mean a straight or branched chain hydrocarbon group containing no unsaturation and having up to and including 8 carbon atoms, such as methyl, ethyl, hexyl, isopropyl, tert.-butyl and so forth. The term "aryl" shall mean phenyl or naphthyl which may be substituted with one of the following groups: halogen (i.e. chlorine, bromine, iodine or fluorine), lower alkyl, hydroxy, lower alkoxy or nitro.

The preparation of compounds of formula I is illustrated in Reaction Scheme A. The structural formulas depicted herein as drawn do not illustrate the relative or absolute stereochemistry of the particular molecules. It should be understood, however, that all of the compounds described herein exist in two relative stereochemical forms: a cis and trans form for compounds of formula II and a threo and erythro form for the remainder of the compounds. To facilitate the description of stereochemical transformations reported herein, the threo and erythro nomenclature as defined stereochemical forms exists as a racemate and as two optical antipodes, and the formulas shown herein are meant to include all of the isomeric and antipodal forms of the compounds depicted.

Epoxyaconitic acid, compound Ia, may be prepared by epoxidation of aconitic acid. Trans-aconitic acid affords threo-epoxide and cis-aconitic acid affords erythro-epoxide. The epoxidation is suitably performed utilizing an epoxidizing agent. Representative epoxidizing agents useful for this reaction include hydrogen peroxide and peracids. Suitable peracids include persulfuric acid, peracetic acid, trifluoroperacetic acid, mono perphthalic acid, perbenzoic acid, metha-chloroperbenzoic acid, and so forth. When hydrogen peroxide is used as the epoxidizing agent, it is preferred to use an epoxidation catalyst in conjunction therewith. A particularly effective epoxidation catalyst is tungstic acid or a salt thereof, particularly an alkali metal salt. The epoxidation is preferably carried out in an aqueous medium, but an organic solvent such an alcohol or ether may be employed as a diluent if desired. Alternatively, the epoxidation may be performed in an inert organic solvent such as a hydrocarbon, a halogenated hydrocarbon or an ether. The reaction temperature is suitably in the range of from about 0°C. to about 100°C. To avoid rearrangement of cis-aconitic acid to trans-aconitic acid prior to epoxidation, it is generally preferred to epoxidize the cis-acid between about 20° and 50°. Cis-aconitic acid anhydride may be suitably employed in place of the acid.

The epoxidation of aconitic esters of formula IIb to epoxy esters of formula Ib may be accomplished in the same manner as described above for the conversion of IIa to Ia.

The interconversion of epoxides Ia and Ib may be accomplished according to standard chemical procedures. For example, the epoxy triacid of formula Ia may be esterified to epoxy triester of formula Ib by contacting said acid with a diazo alkylene such as diazomethane or diazoethane according to well known procedures. Conversly, the triester of formula Ib may be hydrolyzed to the triacid of formula Ia by treatment with base. Suitable bases

REATION SCHEME A

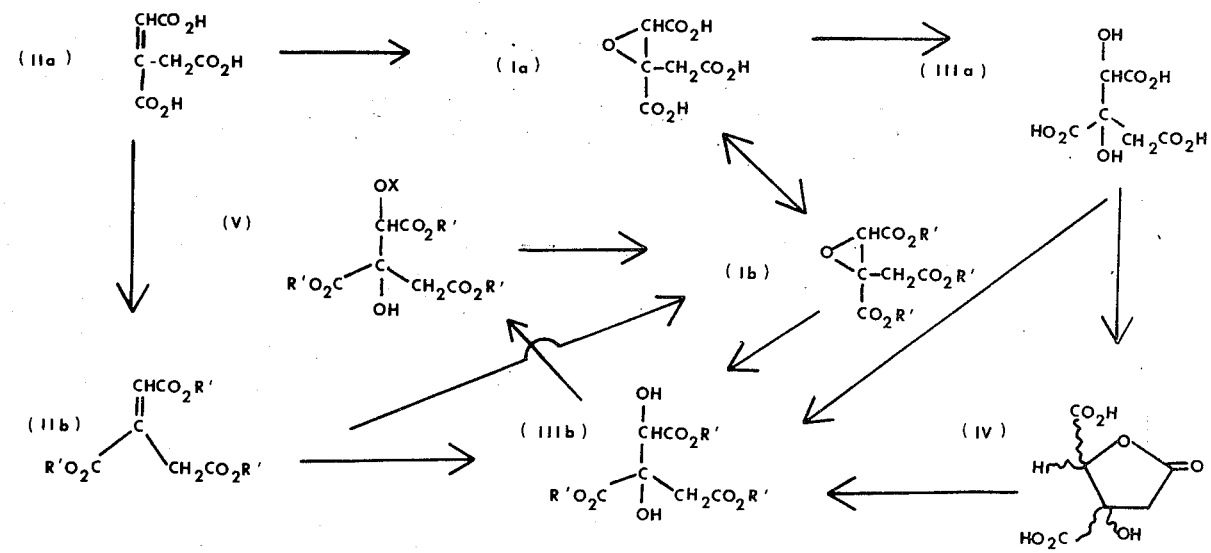

by Cram et al., J. Amer. Chem. Soc., vol. 74, page 5828 (1952) and by Prelog et al., Experinetia, vol. 12, page 81 (1956) has been adopted. Each of these relative wherein R' is lower alkyl and X is lower alkyl sulfonyl or aryl sulfonyl. include for example alkali metal hydroxides, e.g. sodium hydroxide; and alkali metal carbonates or bicarbonates, e.g. sodium carbonate or sodium bicarbonate. The hydrolysis may be carried out in an aqueous alcoholic medium at temperatures ranging from about 0° to about 50°C.

It is generally not preferred to hydrolyze the erythro-epoxy ester of formula Ib to the corresponding erythro-epoxy acid of formula Ia due to the relative lability of the erythro-epoxides as compared with the corresponding threo-epoxides.

An alternative method for the preparation of epoxides of formula Ib involve, as a first step, cis-hydroxylation of aconitic ester IIb. The cis-hydroxylation reaction may be accomplished by utilizing a peroxide in the presence of a hydroxylation catalyst. An especially preferred peroxide is hydrogen peroxide. An especially preferred hydroxylation catalyst is osmium tetroxide. The catalyst may be employed in small quantities as compared with the substrate to be hydroxylated, for example about 0.01 to about 25-mole percent. Approximately 0.1 mole percent of hydroxylation catalyst is preferred. The hydroxylation is suitably performed in any aqueous solvent or solvent mixture. When osmium tetroxide is utilized as a hydroxylation catalyst, it is generally preferred to treat the reaction mixture with a reducing agent before work-up. Suitable reducing agents include sodium sulfite, sodium bisulfite, sodium thiosulfate, and so forth. The reaction temperature of the hydroxylation reaction can be in the range from about 0° to about 100°C. For example, if one utilizes a trans-aconitic ester of formula IIb, then a threo-diol of formula IIIb is produced.

The secondary hydroxyl group of the diol of formula IIIb can then be selectively functionalized to a suitable leaving group OX, wherein X is lower alkyl sulfonyl or aryl sulfonyl, by reaction with the appropriate sulfonyl halide. Suitable sulfonyl halides include methanesulfonyl chloride, p-toluenesulfonyl chloride, p-bromobenzenesulfonyl chloride, p-nitrobenzenesulfonyl chloride, and so forth. Methanesulfonyl chloride is particularly preferred, in which case the compound of formula V is a methanesulfonate (mesylate) ester. The esterification is suitably performed in the presence of a base. Preferred bases are organic amines, e.g. pyridine, triethylamine and so forth. An excess of the amine can serve as the reaction solvent, or an inert organic solvent can serve as a diluent. Suitable diluents include hydrocarbons, e.g. benzene or toluene; ethers, e.g. ethyl ester or tetrahydrofuran; chlorinated hydrocarbons, e.g. methylene chloride; and the like. The temperature of the esterification reaction can be in the range from about −20° to about 50°C. A temperature range from about 0° to about 20°C. is preferred. In the esterification reaction there is no change in stereochemistry at the carbon bearing the secondary hydroxyl. Thus, threo-diol yields threo-mesylate and erythro-diol yields erythro-mesylate.

The sulfonate ester, compound V, is next converted to the epoxide of formula Ib by treatment with base. Suitable bases include, for example, salts of lower alkanoic acids, for example sodium acetate or sodium propionate; alkali metal hydroxides, for example, sodium hydroxide; alkali metal carbonates, for example, sodium carbonate; alkali metal hydrides, for example sodium hydride; and so forth. Choice of solvents and reaction temperatures are not critical and will vary depending upon the nature of the base utilized. Suitable solvents include lower alkanols, e.g. methanol or ethanol; hydrocarbons, e.g. benzene or toluene; and the like. When an alkanol is utilized as solvent, it is preferred to utilize the alkanol corresponding to the R' portion of the compound of formula V so that no transesterification occurs. When utilizing a base stronger than an alkoxide, it is preferred to use an aprotic solvent such as benzene or toluene so that reaction between the base and the solvent does not occur. Suitable combinations of bases and solvents include, for example, sodium hydride in benzene, sodium acetate in methanol, and so forth. The reaction temperature may be in the range from about 20° to about 150°C. A lower reaction temperature may be employed where a stronger base is utilized and vice-versa. This elimination reaction takes place with inversion of configuration. Thus, threo-mesylate affords erythro-epoxide and erythro-mesylate affords thero-epoxide.

Epoxy triacids of formula Ia are readily converted to hydroxy citric acids of formula IIIa which, in turn, form the corresponding γ-lactones of formula IV. Compounds of formulas IIIa and IV are known useful compounds for the control of lipogenesis. See, for example, Belgian Pat. No. 758,122. The conversion of Ia to IIIa may be accomplished by aqueous cleavage of the epoxide in the presence of either acid or base. Generally, the hydroxy citric acid IIIa is converted to the γ-lactone IV in the reaction mixture during work up.

Suitable bases include alkali metal hydroxides, e.g. sodium hydroxide. As mentioned above, the hydrolysis reaction is carried out in an aqueous medium. The reaction temperature can vary from about 20° to about 150°. Generally, a reaction temperature of from about 50° to about 100° is preferred.

An epoxide of formula Ia may also be cleaved by heating alone in an aqueous medium; that is, the epoxy acid itself serves as the acid catalyst. The reaction temperature for this autocatalyzed cleavage can be in the range from about 20° to about 150°, although a temperature of from about 50° to about 100° is generally preferred. It is preferred to carry out the cleavage of the threo-epoxide under basic conditions and the cleavage of the erythro-epoxide under acidic conditions.

In another variation, diol IIIb may be prepared directly from hydroxy citric acid γ-lactone of formula IV by alkanolysis of the lactone ring and concomitant esterification of the carboxyl groups. In this reaction, the γ-lactone is treated with the desired alcohol, R'OH, wherein R' is as above, in the presence of an acid. In a preferred procedure, the alkanol serves as a reaction solvent, although any inert organic solvent can be utilized as a diluent. Suitable acids include mineral acids, e.g. hydrochloric acid or sulfuric acid; organic sulfonic acid, e.g. p-toluene sulfonic acid; and the like. The reaction temperature can be in the range from about 50° to about 100°C. A source of mineral acid can be utilized in place of a mineral acid in this reaction, for example, an acid halide such as acetyl chloride can be added the reaction mixture containing the alcohol solvent to generate hydrogen chloride in situ.

Optically active compounds of formulas I, III and V may be prepared in a number of ways. In one instance, compounds of formula Ia may be resolved directly. One resolution procedure involved fractional crystallization of the salts of compound Ia with an optically active base, for example, an optically active amine. An especially preferred amine for effecting resolution of compounds of formula Ia is cinchonidine.

Alternatively, diol IIIb or sulfonate ester V can be resolved. Optically active products may also be prepared starting with an optically active hydroxy citric acid of formula IIIa or its γ-lactone of formula IV.

The compounds of formula I are useful for inhibiting fatty acid synthesis in biological systems. The biological systems in which the compounds of the present invention may be used include those which contain citrate cleavage enzyme. Preferred biological systems are mammals, particularly non-ruminating mammals.

The inhibition of fatty acid synthesis in biological systems, by the use of the compounds of the present invention is believed to arise from the inhibition of citrate cleavage enzyme contained in such systems. The cleavage of citrate is catalyzed by citrate cleavage enzyme according to the stoichiometry: citrate + CoA + ATP → acetyl − CoA + oxaloacetate + ATP + $P_i$.

In the conversion of carbohydrates and various amino acids to fat by non-ruminating mammals, citrate is the major source of acetyl co-enzyme A which is utilized for the synthesis of fatty acids. Citrate is formed in the mitochondria by the citrate synthase reaction. It is then metabolized via the citric acid cycle. Under conditions when energy intake exceeds energy demand, some citrate is diverted to the extra-mitochondrial space of the cell where it is used for fatty acid synthesis, that is to say, for energy storage. The novel compounds of formula I of the present invention are thus useful in the treatment of obesity and in the correction of lipid abnormalities. The epoxides of formula Ia may also be utilized in the form of their pharmaceutically acceptable non-toxic basic salts. Preferred salts for this purpose include the alkali metals, e.g. sodium or potassium; the alkaline earth metals, e.g. calcium; or complex salts such as ammonium or substituted ammonium salts such as a mono-, or di- or tri-alkylammonium salt or a mono-, di- or tri-hydroxyalkylammonium salt. The compounds can be made up in the form of conventional pharmaceutical preparations; for example, the aforesaid compounds can be mixed with organic or inorganic inert pharmaceutical carriers suitable for parenteral or enteral administration such as, for example, water, gelatin, lactose, starch, magnesium stearate, talc, vegetable oil, gums or the like. They can be administered in conventional pharmaceutical forms, e.g. solid forms, for example, tablets, capsules, dragees, suppositories, or the like; or in liquid forms, for example, solution, suspensions, or emulsions. Moreover, the pharmaceutical compositions containing the compounds of this invention can be subjected to the conventional pharmaceutical expedients, such as sterilization, and can contain conventional pharmaceutical excipients such as preservatives, stabilizing agents, emulsifying agents, salts for the adjustment of osmotic pressure or buffers. The compositions can also contain other therapeutically active materials.

A suitable pharmaceutical dosage unit can contain from about 15 to 600 mg. of the aforesaid compound.

Suitable parenteral dosage regiments in mammals comprise from about 1 mg/kg to about 25 mg/kg per day. However, for any particular subject, specific dosage regimens should be adjusted according to the individual need and the professional judgment of the person administering or supervising the administration of the aforesaid compounds. It is to be understood that the dosages set forth herein are exemplary only; that they do not, to any extent, limit the scope or practice of the invention.

The present invention may be more clearly illustrated by the following examples. All the temperatures are stated in degrees Centigrade.

EXAMPLE 1

(±)-Threo-1,2-epoxy-1,2,3-propanetricarboxylic acid [(±)-threoepoxyaconitic acid]

A solution of trans-aconitic acid (10 g.) and tungstic acid (2.0 g.) in 1N sodium hydroxide solution (143 ml.) containing hydrogen peroxide (30%; 6 ml.) was stirred at 85° for two hours. The solution was cooled, 10N hydrochloric acid (15.5 ml.) was added and then was extracted exhaustively with ether using a liquid-liquid extractor. Evaporation of the ether layer furnished a white solid which on crystallization from ether-methylene chloride gave epoxide, mp 167°–169°. A second crop, mp 159°–164° was isolated from the mother liquors. The analytically pure specimen was obtained from the same solvent system, mp 168°–170°.

Anal. Calcd. for $C_6H_6O_7$: C, 37.91; H, 3.18 Found: C, 37.22; H, 3.69.

EXAMPLE 2

Resolution of (±)-threo-1,2-epoxy-1,2,3-propanetricarboxylic acid [(±)-threo-epoxyaconitic acid]

A solution of (±)-threo-epoxyaconitic acid (3.0 g.) in methanol (120 ml.) was heated to reflux. To the boiling solution cinchonidine (9.0 g.) was added followed by ethyl acetate (~ 250 ml.) and heating was continued until crystallization of the salt had started. The solution was allowed to cool and the cinchonidine salt was collected by filtration and washed with ethyl acetate (20 ml.) (Crop A). The filtrate was concentrated and two additional crops of crystalline material were obtained (Crops B and C). The mother liquors were evaporated to dryness in vacuo to give a white solid (Crop D). Crops A and D were processed as below. Crops B and C were combined for recycling.

i. (+)-Threo-epoxyaconitic acid

Crop A was dispersed in chloroform and extracted with 1N sodium hydroxide solution (1 × 25 ml.; 1 × 10 ml.). The combined basic extracts were washed with chloroform (2 × 10 ml.) then were acidified with 1N hydrochloric acid (36 ml.) and concentrated in vacuo. The resulting residue was extracted with hot ethyl acetate and the residual sodium chloride was removed by filtration. The filtrate was concentrated under reduced pressure and crystallization of the product from ethyl acetate-carbon tetrachloride gave the epoxide as a carbon tetrachloride solvate. Air drying furnished the dextrarotatory threo-epoxide as the monohydrate, mp 108°–112°; $[\alpha]_D^{25}$ + 63.1° (c, 1.0, $H_2O$).

Anal. Calcd. for $C_6H_6O_7 \cdot H_2O$: C, 34.63; H, 3.87. Found: C, 34.91; H, 3.81.

ii. (−)-Threo-epoxyaconitic acid

Crop D was dispersed in chloroform (40 ml.) aand extracted with two portions (35 ml. and 15 ml.) of 1N sodium hydroxide solution. The combined aqueous extracts were washed with chloroform (2 × 10 ml.) then were acidified with 1N hydrochloric acid (51 ml.) and evaporated to dryness in vacuo. Trituration of the residue with ethyl acetate and evaporation of the extracts gave an oil which on fractional crystallization from ethyl acetate-carbon tetrachloride gave the solvated levorotatory epoxide. After air drying, the monohydrate had mp 108°–112°; $[\alpha]_D^{25}$ − 62.5° (c, 1.0, $H_2O$).

Anal. Calcd. for $C_6H_6O_7 \cdot H_2O$: C, 34.63; H, 3.89. Found: C, 34.91; H, 3.74.

EXAMPLE 3

(+)-Erythro-hydroxycitric acid, γ lactone (Hibiscus acid) from (+)-threo-epoxyaconitic acid]

A solution of the dextrarotatory epoxide prepared as in Example 2 (1.9 g.: 30 meq.) in 1N sodium hydroxide (30 ml.) was refluxed under nitrogen for three days. The reaction mixture was then cooled to ∼ 80° and a solution of calcium chloride (2.6 g.) in water (5 ml.) was added rapidly with stirring. The resulting white precipitate was collected by filtration and washed well with water then was dissolved in the minimum amount of 1N hydrochloric acid (∼ 15 ml.). The solution was passed through a column of cationic exchange resin (Amberlight IRA 120; 30 ml.). The acidic eluents were evaporated to dryness and then the residue was heated on a steam bath to induce crystallization to give essentially pure lactone. The residue was dissolved in ethyl acetate and the pale yellow solution was decolorized with charcoal. Two crystallizations from ethyl acetate-carbon tetrachloride furnished analytically pure hibiscus acid, mp 187°-8°; $[\alpha]_D^{25}$ + 109° (c, 1.0, $H_2O$), identical with authentic material.

EXAMPLE 4

(±)-Erythro-1,2-epoxy-1,2,3-propanetricarboxylic acid [(±)-erythro-epoxyaconitic acid]

A solution of tungstic acid (1.3 g.) in hydrogen peroxide (30%; 6.6 ml.) was added to cis-aconitic anhydride (10.1 g.) in water (115 ml.) and the stirred reaction mixture was placed in an oil bath previously heated to 40°. The reaction was maintained at this temperature for 90 minutes then it was placed in a liquid-liquid extractor and continuously extracted with ether. Concentration of the extract obtained after 5.5 hours gave an oil. Fractional crystallization (ethyl acetate-carbon tetrachloride) of this material gave the erythro-epoxide, mp 176°–178° and a second crop, mp 168°–172°. The material obtained from continuous extraction overnight furnished additional epoxide, mp 173°–176°.

The pure (±)-erythro-epoxide was obtained by crystallization from ethyl acetate-carbon tetrachloride, mp 175.5°–178°.

Anal. Calcd. for $C_6H_6O_7$: C, 37.91; H, 3.18 Found: C, 37.96; H, 3.44.

EXAMPLE 5

(±)-Threo-hydroxycitric acid, γ lactone from (±)-erythro-epoxyaconitic acid

A solution of the erythro-epoxide prepared as in Example 4 (190 mg.) in water (3 g.) was heated on a steam bath for 4.5 hours. The solvent was removed in vacuo and the oily residue was heated on a steam bath for 30 min. to give 190 mg. of (±)-threo-hydroxy-citric acid γ lactone. A small amount was esterified using diazomethane in ether. Examination of the resulting ester showed it to be essentially pure (±)-threo-hydroxycitric acid, γ lactone, dimethyl ester.

EXAMPLE 6

Trans-trimethyl aconitate

Acetyl chloride (100 ml.) was added to a cooled solution of trans-aconitic acid (100 g.) in methanol (1500 ml.). The solution was refluxed for 3.5 hours then was cooled to room temperature. Sufficient pyridine (86 ml.) was added to neutralize the reaction mixture, then most of the solvent was removed in vacuo. The resulting oil was dissolved in methylene chloride and the solution was washed in turn with dilute hydrochloric acid solution, water, dilute sodium bicarbonate solution and finally water. The methylene chloride extract was dried ($MgSO_4$) and concentrated under reduced pressure to give the trimethyl ester as a pale yellow oil. This material was distilled under vacuum to afford the triester as a colorless liquid (bp 110°–112°; 0.6 mm).

EXAMPLE 7

(±)-Threo-1,2-dihydroxy-1,2,3-propanetricarboxylic acid, trimethyl ester

To a solution of trans-trimethyl aconitate (57 g.) in acetone (300 ml.) and water (75 ml.) was added a solution of osmium tetroxide in acetone (1%; 7.5 ml.) followed by hydrogen peroxide (30%; 37 ml.). The stirred solution was brought to reflux and was maintained at this temperature for four hours. The reaction mixture was cooled and left at room temperature overnight, then enough sodium bisulfite was added (∼ 1 g.) to discharge the remaining oxidant. The solvent was removed in vacuo and the residual oil was dissolved in water (300 ml.) and extracted with ether (4 × 250 ml.). The ether layers were backwashed in turn with water (100 ml.). Sodium chloride (130 g.) was dissolved in the combined aqueous layers which were then extracted with methylene chloride (5 × 300 ml.). The combined methylene chloride extracts were dried ($MgSO_4$) and evaporated to give a viscous oil. Crystallization of the oil from ether-hexane afforded 29.3 g. of the (±)-threo-diol, mp 74°–76°. The analytical sample was obtained from the same solvent mixture, mp 75°–76°.

Anal. Calcd. for $C_9H_{14}O_8$: C, 43.20; H, 5.64. Found: C, 43.42; H, 5.68.

EXAMPLE 8

(±)-Threo-1-mesyloxy-2-hydroxy-1,2,3-propanetricarboxylic acid, trimethyl ester

Methanesulfonyl chloride (4.5 ml.; 57 mmol) was added to a cooled (∼5°) solution of the (±)-threo-diol prepared as in Example 7 (12.0 g.; 48 mmol) in pyridine (100 ml.) and the mixture was kept at 0°–5° for 2 hours. Several chips of ice were then added to the reaction mixture and after five minutes it was poured into an ice-water mixture (500 ml.) containing concentrated hydrochloric acid (110 ml.). The pale yellow acidic solution was extracted with methylene chloride (3 × 200 ml.) and the organic layers were washed in turn with brine and with a saturated sodium bicarbonate solution. The dried ($MgSO_4$) methylene chloride extracts were decolorized (charcoal) and then evaporated to dryness. Crystallization of the residue from methylene chloridehexane gave pale yellow crystals, mp 92°–94°. The analytically pure mesylate was obtained by crystallization from ethyl acetatehexane, mp 91°–93°.

Anal. Calcd. for $C_{10}H_{16}O_{10}S$: C, 36.56; H, 4.91; S, 9.76 Found: C, 36.41; H, 4.95; S, 9.72.

EXAMPLE 9

(±)-Erythro-1,2-epoxy-1,2,3-propanetricarboxylic acid, trimethyl ester [(±)-erythro-epoxyaconitic acid, trimethyl ester]

A solution of (±)-threo-mesylate prepared as in Example 8 (56.0 g.) in methanol (800 ml.) containing sodium acetate (28.0 g.) was refluxed for 100 minutes and then was cooled to room temperature. A copious precipitate that had formed during the reaction was removed by filtration and discarded and the filtrate was concentrated in vacuo. The residue was taken up in chloroform and the solution was washed in turn with brine and dilute sodium bicarbonate solution. The dried ($MgSO_4$) organic layer was evaporated under reduced pressure and the resulting oil was crystallized from ether-hexane to give the epoxide, mp 54°–57°. Analytically pure epoxide was obtained from ether-hexane, mp 55°–57°.

Anal. Calcd. for $C_9H_{12}O_7$: C, 46.56; H, 5.21 Found: C, 46.66; H, 5.16.

EXAMPLE 10

(±)-Threo-1,2-epoxy-1,2,3-propanetricarboxylic acid, trimethyl ester [(±)-threo-epoxyaconitic acid, trimethyl ester ]

Acetyl chloride (20 ml.) was added carefully to a solution of (±)-threo-epoxyaconitic acid (20 g.) in methanol (400 ml.) previously cooled by means of an ice-water bath. The solution was refluxed for one hour, then was cooled and enough pyridine (25 ml.) was added to neutralize the reaction mixture. The solvent was removed in vacuo and the resulting oil was partitioned using methylene chloride and water. The methylene chloride layer was washed with brine, 0.5 N hydrochloric acid solution and finally dilute sodium bicarbonate solution. The aqueous layers were backwashed in turn with methylene chloride, then the combined organic extracts were dried ($MgSO_4$) and concentrated under reduced pressure to give a viscous oil. Crystallization of the crude product from ether-hexane furnished essentially pure epoxide, mp ~ 34°. The analytical sample was obtained from the same solvent, mp 38°–40°.

Anal. Calcd. for $C_9H_{12}O_7$: C, 46.56; H, 5.21 Found: C, 46.68; H, 5.03.

EXAMPLE 11

(±)-Erythro-1,2-dihydroxy-1,2,3-propanetricarboxylic acid, trimethyl ester

To a solution of (±)-erythro-hydroxycitric acid, γ lactone; (21 g.) in methanol (400 ml.) was added acetyl chloride (21 g.). The solution was brought to reflux and maintained at this temperature for 90 minutes, then was cooled and left overnight at room temperature. Enough pyridine (19 ml.) was added to neutralize the reaction mixture then the solvent was removed under reduced pressure. The resulting syrup was dissolved in water (350 ml.) and the solution was extracted with ether (5 × 100 ml.). The ether extracts were backwashed in turn with water (2 × 100 ml.). Sodium chloride (~ 125.g) was dissolved in the combined aqueous layers and the solution was extracted with methylene chloride (1 × 350 ml.; 3 × 125 ml.). The methylene chloride extracts were washed in turn with brine and with saturated sodium bicarbonate solution. The dried ($MgSO_4$) methylene chloride extracts were concentrated in vacuo to give the trimethyl ester as a viscous oil.

EXAMPLE 12

(±)-Erythro-1-mesyloxy-2-hydroxy-1,2,3-propanetricarboxylic acid, trimethyl ester Crude (±)-erythro-diol (23.7 g.) prepared as in example 11 was dissolved in pyridine (200 ml.) and to the cooled (~ 5°) solution methanesulfonyl chloride (7.2 ml.) was added. The reaction mixture was stored at 0°–5° for 150 minutes then it was poured into an ice-water mixture (~ 1 l.) containing concentrated hydrochloric acid (210 ml.). The resulting red solution was extracted with methylene chloride (4 × 200 ml.) and then the organic layers were washed in turn with brine and with saturated sodium bicarbonate solution. The combined methylene chloride extracts were dried ($MgSO_4$) then decolorized (charcoal) and concentrated under reduced pressure to give a pale yellow oil. Trituration of the residue with ether furnished crude mesylate which on recrystallization from methylene chloride-hexane gave 21.7 g. of pure material, mp 104°–106°.

Anal. Calcd. for $C_{10}H_{16}O_{10}S$: C, 36.58; H, 4.91; S, 9.76. Found: C, 36.63; H, 4.85; S, 9.81.

EXAMPLE 13

(−)-Threo-1,2-dihydroxy-1,2,3-propanetricarboxylic acid, trimethyl ester

To a cooled solution of (+)-threo-hydroxycitric acid γ lactone ("garcinia" acid; 10 g.) in methanol (200 ml.) was added acetyl chloride (10 ml.). The solution was heated at reflux for 90 minutes then cooled to room temperature. Sufficient pyridine (9.0 ml.) was added to neutralize the reaction mixture then the solvent was removed in vacuo. The oily residue was dispersed in brine and extracted with methylene chloride (5 × 100 ml.). The organic extracts were washed in turn with 1N hydrochloric acid solution and with saturated sodium bicarbonate solution. The extracts were combined, dried ($MgSO_4$) and concentrated under reduced pressure to give crude diol trimethyl ester as an oil.

EXAMPLE 14

1(S),2(S)-1-mesyloxy-2-hydroxy-1,2,3-propane tricarboxylic acid, trimethyl ester [(−)-threo-mesylate]

Methane-sulfonyl chloride (3.55 ml.) was added to a solution of crude (−)-threo-diol prepared as in Example 13 (11.7 g.) in pyridine (100 ml.) previously cooled to 5°–10°. The reaction mixture was kept at 0°–5° for 2.5 hours then was poured into a stirred ice-water mixture containing 100 mls. of concentrated hydrochloric acid. The resulting solution was extracted with methylene chloride (4 × 200 ml.) and the extracts were washed in turn with brine (1 ×) and saturated sodium bicarbonate (2 ×). The combined extracts were dried ($MgSO_4$), decolorized (charcoal) and concentrated in vacuo to give the crude mesylate as an oil. Trituration of the oil with ether afforded a solid, mp 83°–86°. Recrystallization of this material from methylene chloride-hexane gave the mesylate, mp 89°–91°. The analytically pure sample was obtained by crystallization from ether-hexane, mp 89°–91°; $[\alpha]_D^{25} - 8.38°$ (c, 0.75, $CH_3OH$).

Anal. Calcd. for $C_{10}H_{16}O_{10}S$: C, 36.58; H, 4.91; S, 9.76 Found: C, 36.78; H, 4.97; S, 9.73.

EXAMPLE 15

1(R),2(S)-1,2-Epoxy-1,2,3-propanetricarboxylic acid, trimethyl ester [(−)-erythro-epoxyaconitic trimethyl ester]

A solution of the optically active mesylate prepared as in Example 14 (15 g.) in methanol (200 ml.) containing sodium acetate was stirred under reflux for 2 hours. The reaction mixture was cooled and most of the methanol was evaporated under reduced pressure. The residue was taken up in chloroform and the chloroform solution was washed in turn with brine, sodium bicarbonate solution and finally brine. The organic layer was dried and evaporated in vacuo to give an oil. Crystallization of the product from ether gave the epoxide, mp 64°–5°. The same solvent furnished the analytically pure sample, mp 64°–5°; $[\alpha]_D^{25} - 34.6°$ (c, 1.07, $CH_3OH$).

Anal. Calcd. for $C_9H_{12}O_7$: C, 46.56; H, 5.21 Found: C, 46.71; H, 5.08

EXAMPLE 16

Capsule Formulation

|  | Per Capsule |
|---|---|
| (±)-Threo-epoxyaconitic acid | 250 mg. |
| Lactose | 60 mg. |
| Corn Starch | 35 mg. |
| Magnesium Stearate | 5 mg. |
| Total Weight | 350 mg. |

PROCEDURE:
1) All of the ingredients were mixed until thoroughly blended in a suitable size container.
2) The powder was filled into No. 2, two piece, hard shell gelatin capsules to an approximate fill weight of 350 mg. using a Parke Davis capsulating machine. (Any similar type machine may be used.)

EXAMPLE 17

Tablet Formulation

|  | Per Tablet |
|---|---|
| (±)-Threo-epoxyaconitic acid | 200 mg. |
| Dicalcium Phosphate Dihydrate, Unmilled | 235 mg. |
| Corn Starch | 70 mg. |
| FD & C Yellow No. 5 - Aluminum Lake 25% | 2 mg. |
| Durkee 117 | 25 mg. |
| Calcium Stearate | 3 mg. |
| Total Weight | 535 mg. |

PROCEDURE:
1) All the ingredients were mixed thoroughly and Fitzed (Model D) using a No. 1A screen, medium speed.
2) The mixture was remixed and slugged.
3) The slugs were screened on an Oscillator through a No. 14 mesh screen and compressed on an "E" machine.

EXAMPLE 18

Capsule Formulation

|  | Per Capsule |
|---|---|
| (±)-Threo-epoxyaconitic acid | 50 mg. |
| Lactose, USP | 125 mg. |
| Corn Starch, USP | 30 mg. |
| Talc, USP | 5 mg. |
| Total Weight | 210 mg. |

-continued
Capsule Formulation

PROCEDURE:
1) (±)-Threo-epoxyaconitic acid was mixed with lactose and corn starch in a suitable mixer.
2) The mixture was further blended by passing through a Fitzpatrick Comminuting Machine with a No. 1A screen with knives forward.
3) The blended powder was returned to the mixer, the talc added and blended thoroughly.
4. The mixture was filled into No. 4 hard shell gelatin capsules on a Parke Davis capsulating machine.

EXAMPLE 19

Tablet Formulation

|  | Per Tablet |
|---|---|
| (±)-Threo-epoxyaconitic acid | 25 mg. |
| Dicalcium Phosphate Dihydrate, Unmilled | 175 mg. |
| Corn Starch | 24 mg. |
| Magnesium Stearate | 1 mg. |
| Total Weight | 225 mg. |

PROCEDURE:
1) (±)-Threo-epoxyaconitic acid and corn starch were mixed together and passed through a No. 00 screen in Model "J" Fitzmill with hammers forward.
2) This premix was then mixed with dicalcium phosphate and one-half of the magnesium stearate, passed through a No. 1A screen in Model "J" Fitzmill with knives forward, and slugged.
3) The slugs were passed through a No. 2A plate in Model "D" Fitzmill at slow speed with knives forward, and the remaining magnesium stearate was added.
4) The mixture was mixed and compressed.

EXAMPLE 20

Tablet Formulation

|  | Per Tablet |
|---|---|
| (±)-Threo-epoxyaconitic acid | 100 mg. |
| Lactose, USP | 202 mg. |
| Corn Starch, USP | 80 mg. |
| Amijel B011* | 20 mg. |
| Calcium Stearate | 8 mg. |
| Total Weight | 410 mg. |

PROCEDURE:
1) (±)-Threo-epoxyaconitic acid, lactose, corn starch, and Amijel B011 were blended in a suitable mixer.
2) The mixture was granulated to a heavy paste with water and the moist mass was passed through a No. 12 screen. It was then dried overnight at 110°F.
3) The dried granules were passed through a No. 16 screen and transferred to a suitable mixer. The calcium stearate was added and mixed until uniform.
4) The mixture was compressed at a tablet weight of 410 mg. using tablet punches having a diameter of approximately ⅜". (Tablets may be either flat or biconvex and may be scored if desired).

*A prehydrolyzed food grade corn starch. Any similar prehydrolyzed corn starch may be used.

EXAMPLE 21

Tablet Formulation

|  | Per Tablet |
|---|---|
| (±)-Threo-epoxyaconitic acid | 500 mg. |
| Corn Starch | 30 mg. |
| Lactose | 88 mg. |
| Gelatin | 12 mg. |
| Talcum | 15 mg. |
| Magnesium Stearate | 5 mg. |
| Total Weight | 650 mg. |

PROCEDURE:
1) (±)-Threo-epoxyaconitic acid and lactose were thoroughly mixed in suitable blending equipment and granulated with

-continued
Tablet Formulation a 10% gelatin solution.
2) The moist mass was passed through a No. 12 screen, and the granules were dried on paper lined trays overnight.
3) The dried granules were passed through a No. 14 screen and placed in a suitable mixer. The talcum and magnesium stearate were added and blended.
4) The granulation was compressed into tablets weighing approximately 650 mg. each, using punches having an approximate diameter of 12.7 mm(½"). The final tablet thickness was about 5.1 mm.

EXAMPLE 22

Measurement of lipogenesis in vivo

Female Charles River rats weighing from 120–150 g. were provided free access to water and were fed a commercial diet prior to the initiation of the experiment. Each experimental group of animals were prefasted two days and then meal-fed a single meal daily from 9-12 a.m. The meal consisted of a 70% glucose fat-free diet (G-70) containing 70% glucose, 24% vitamin-free casein, 5% salt and 1% vitamin, to which 40 g. cellulose was added per kilogram.

On the last day of feeding, at a specified time before initiation of the meal, the epoxide derivative in ASV of the composition sodium chloride 0.9%, carboxy methyl cellulose 0.5%, benzyl alcohol 0.86% and tween 80 (polyoxyethylene sorbitan monoleate) 0.39% or in saline solution was administered. At a specified time after feeding, rats were lightly anaesthetized with Penthrane (methoxyflurane) and injected in the tail vein with 0.25 ml. of a solution with the following composition: 12.3 mg. alanine, 5μC$^{14}$ C-alanine (specific activity = 156 mC/mmole) as fatty acid precursor and 30.6 mg. α-ketoglutarate as a transaminase acceptor dissolved in saline pH 7.4 – 7.6. After 30 minutes, rats were sacrificed by decapitation and their livers were excised, rapidly weighed, minced in 15 ml. water and homogenized in a Potter-Elvehjem homogenizer with 5 strokes of a drill press-driven teflon pestle. Duplicate 3-ml. aliquots of whole liver homogenates were added to tubes containing 2.1 ml. 5N NaOH and saponified with 2.6 ml. 5N H$_2$SO$_4$ and extracted twice with 5 ml. of petroleum ether (bp 40°–60°C.). Supernatants were added directly to glass counting vials, evaporated to dryness and 10 ml. of toluene-PPO-POPOP scintillation fluid was added. Samples were analyzed for absolute activity in a Packard Tri-carb scintillation counter.

Resulting data was expressed as nanomoles $^{14}$C-alanine incorporated/gram of tissue/30 minutes.

Inhibition of in vivo rates of lipogenesis by oral administration of epoxides[1]

| Epoxide[2] | Lipogenesis | |
|---|---|---|
| | nanomoles $^{14}$C-alanine/ g. liver/30 min. | Percent Inhibition |
| ASV | 1022.4 ± 58.7(21)[3] | 0 |
| (±)-Threo-epoxyaconitic acid | 280.6 ± 81.9(5) | 73 |
| (−)-Threo-epoxyaconitic acid | 198.7 ± 32.5(5) | 81 |
| (+)-Threo-epoxyaconitic acid | 364.8 ± 72.0(5) | 64 |
| (±)-Erythro-epoxyaconitic acid | 808.5 ± 189.8(5) | 20 |
| (−)-Erythro-epoxyaconitic acid trimethyl ester | 624.2 ± 175.6(5) | 39 |

[1]Rats were prefasted 2 days, meal-fed the G-70 diet for 12 days and assayed in vivo immediately after the completion of the last meal.
[2]Derivatives were suspended in ASV (2.63 mmoles/kg) and given by stomach tube 60 min. before feeding.
[3]Mean ± SEM for the number of rats indicated in parentheses.

Inhibition of in vivo rate of lipogenesis by orally administered (±)-threo-epoxy-aconitic acid[1]

| Group | Dose administered (in saline solution) mmoles/kg | Lipogenesis nanomoles $^{14}$C-alanine/ g. liver/30 min. | Percent Inhibition |
|---|---|---|---|
| 1 | — | 1091.4 ± 55.6(31)[2] | 0 |
| 2 | 5.26 | 222.0 ± 41.8(15) | 80 |
| 3 | 2.63 | 372.2 ± 66.7(19) | 66 |
| 4 | 1.32 | 668.7 ± 129.0(9) | 39 |
| 5 | 0.66 | 769.2 ± 52.1(9) | 29 |

[1]Rats were prefasted for 2 days and meal-fed the G-70 diet for 9 days. On the last day of feeding they were given the derivatives 60 min. prior to the meal and assayed in vivo 5 hours after the initiation of feeding.
[2]Mean ± SEM for the number of rats indicated in parentheses.

Effect of pre-treatment with (±)-threo-epoxyaconitic acid on the rate of in vivo lipogenesis[1]

| Group | Concentration (in saline solution) mmoles/kg | Administration Time (hr. before feeding) hours | In vivo lipogenesis nanomoles $^{14}$C-alanine/ g. liver/30 min. | Percent Inhibition |
|---|---|---|---|---|
| A | — | 16 | 1255.2 ± 123.5(8)[3] | 0 |
| A | 5.26 | 16 | 495.1 ± 63.3(3) | 60 |
| A | 2.63 | 16 | 1573.2 ± 163.1(4) | +25 |
| B | — | 16 & 12[2] | 1189.1 ± 127.3(5) | 0 |
| B | 5.26 | 16 & 12 | 486.2 ± 104.4(5) | 59 |
| B | 2.63 | 16 & 12 | 616.9 ± 173.5(5) | 48 |

[1]Rats were prefasted 2 days and meal-fed the G-70 diet for 10 days. They were assayed in vivo 5 hours after initiation of feeding.
[2]Derivatives were given 16 hours before feeding (day 9) and 12 hours before feeding (day 10).
[3]Mean ± SEM for number of rats indicated in parentheses.

We claim:
1. A compound of the formula

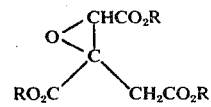

having the threo-configuration wherein all R groups are hydrogen
and the optical antipodes and pharmaceutically acceptable salts thereof.
2. The (+) antipode of the compound of claim 1.
3. The (−) antipode of the compound of claim 1.

* * * * *